United States Patent
Chapuis

(10) Patent No.: US 8,822,733 B2
(45) Date of Patent: Sep. 2, 2014

(54) INTERMEDIATES FOR THE PREPARATION OF BETA-SANTALOL

(75) Inventor: Christian Chapuis, Geneva (CH)

(73) Assignee: Firmenich SA, Geneva (CH)

( * ) Notice: Subject to any disclaimer, the term of this patent is extended or adjusted under 35 U.S.C. 154(b) by 0 days.

(21) Appl. No.: 13/981,897

(22) PCT Filed: Feb. 8, 2012

(86) PCT No.: PCT/EP2012/052111
§ 371 (c)(1),
(2), (4) Date: Jul. 25, 2013

(87) PCT Pub. No.: WO2012/110375
PCT Pub. Date: Aug. 23, 2012

(65) Prior Publication Data
US 2013/0310609 A1    Nov. 21, 2013

(30) Foreign Application Priority Data
Feb. 16, 2011    (EP) .................................. 11154605

(51) Int. Cl.
*C07C 45/61* (2006.01)
*C07C 29/14* (2006.01)
*C07C 33/12* (2006.01)

(52) U.S. Cl.
USPC ........................................ 568/445; 568/820

(58) Field of Classification Search
USPC ................................................ 568/445, 820
See application file for complete search history.

(56) References Cited

U.S. PATENT DOCUMENTS 4,197,411 A    4/1980    Hoffmann et al.

FOREIGN PATENT DOCUMENTS

| EP | 10213 B1 | 11/1981 |
| WO | WO 2005/037243 A1 | 4/2005 |
| WO | WO 2008/120175 A1 | 10/2008 |
| WO | WO 2009/141781 A1 | 11/2009 |

OTHER PUBLICATIONS

Sprott & Corey, Org. Lett., 2003, 5, 2465.
Suzuki et al., Tetrah. Lett., 2002, 43, 7531-7533.
Takai et al., Tetrah. Lett., 1985, vol. 26, n° 45, 5585-5588.
Furuta, Yamamoto et al., J. Org. Chem., 1989, 54, 1481.
Furuta, Yamamoto et al., Tetrah. Lett., 1989, 30, 7231.
Ishihara & Yamamoto, J. Am. Chem. Soc., 1994, 116, 1561.
Zhou, Corey et al., Org. Lett., 2003, vol. 5, n° 21, 3979-3982.
Hu, Corey et al., J. Am. Chem. Soc., 2004, 126, 13708.
Huang, Rawal et al., J. Am. Chem. Soc., 2000, 122, 7843.
Huang, Rawal et al., J. Am. Chem. Soc., 2002, 124, 5950.
Huang, Rawal et al., Org. Lett., 2002, 4, 1163.
Ishihara et al., J. Am. Chem. Soc., 1998, 120, 6920.
Kaino et al., Chem. Commun., 2009, 1956.
Krotz, Tetrah. Asymmetry, vol. 1, n° 8, 1990, 537-540.
Kubota et al., Tetrahedron 62 (2006) 11397-11401.
Liu, Corey et al., J. Am. Chem. Soc., 2007, 129, 1498.
Matsumura et al., Tetrah. Lett., 48 (2007), 1265-1268.
Mukherjee, Corey et al., Org. Lett., 2010, 12, 1836.
Oppolzer et al., Tetrah. Lett., 1983, vol. 24, n° 43, 4665-4668.
Pauling et al., Helv. Chim. Acta, 1976, 59, 1233.
Ryu, Corey et al., J. Am. Chem. Soc., 2002, 124, 9992.
Saito et al., Tetrah. Lett., 1995, vol. 36, n° 49, 9003-9006.
Shibasaki, J. Org. Chem., 1988, 53, 1227.
Simmons, Helv. Chim. Acta, 1988, 71, 1000.
Snyder & Corey, J. Am. Chem. Soc., 2006, 128, 740.
Solas et al., J. Org. Chem., 1983, 48, 1988.
Sonawane et al., J. Org. Chem., 1991, 56, 1434.
International Search Report and Written Opinion, application PCT/EP2012/052111, mailed Mar. 28, 2012.
Baumann, Hoffmann et al., J. Lieb. Ann. Chem. 1979, n° 6, 743-750.
Boeckman et al., Helv. Chim. Acta, 2002, 85, 4532.
Christenson et al., J. Org. Chem., 1979, 44, 2012.
Ernan, Kheifits et al., Tetrah. Lett., 1976, 17, n° 34, 2981-2984.
Fehr et al., Angew. Chem. Intl. Ed. 2009, 48, 7221.
Fernandes et al., Eur. J. Org. Chem., 2010, 4306-4311.
Hayashi, Corey et al., J. Am. Chem. Soc., 1996, 118, 5502.
Herbert Kretschmar et al., Tetrah. Lett., 1970, 1, 41-44.
Hong & Corey, J. Am. Chem. Soc., 2006, 128, 1346.

*Primary Examiner* — Sikarl Witherspoon
(74) *Attorney, Agent, or Firm* — Winston & Strawn LLP

(57) ABSTRACT

The present invention concerns a process for the preparation of a compound of formula (I) in the form of any one of its stereoisomers or mixtures thereof, and wherein the dotted line may represents an additional bond and $R^a$ represents a hydrogen atom or a $Si(R^b)_3$ or $(R^b)_2COH$ group, each $R^b$ representing $C_{1-6}$ alkyl group or a phenyl group. The invention concerns also the compound (I) as well as its use for the synthesis of β-santalol or of derivatives thereof.

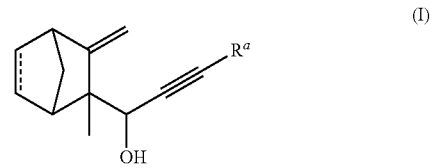

(I)

8 Claims, No Drawings

INTERMEDIATES FOR THE PREPARATION OF BETA-SANTALOL

TECHNICAL FIELD

The present invention relates to the field of organic synthesis and more specifically it concerns a process for the preparation of a compound of formula

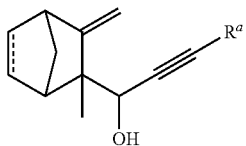
(I)

as defined further below. The invention concerns also the compound (I) as well as its precursors and the process for manufacturing compound (I). Furthermore, it concerns also the use of compound (I) for the synthesis of β-santalol or of derivatives thereof.

PRIOR ART

The compounds of formula (I) are novel compounds, and are useful starting materials for the preparation of β-santalol, and derivatives thereof, in a short and effective manner.

The β-santalol, and derivatives thereof, are well known perfuming ingredients, some of which of particular relevance. Therefore, there is always a need for alternative synthesis to produce them.

To the best of our knowledge, several processes have been reported in the literature for the preparation of β-santalol and derivatives thereof. One may cite the following references: U.S. Pat. No. 4,197,411, EP 10213 or WO 09/141,781.

All of said processes use as key intermediate a compound of formula

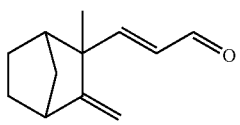
(A)

or the similar, and propose various approaches to such intermediate.

In particular, U.S. Pat. No. 4,197,411 and EP 10213 disclose the closest analogues of the present invention's compounds, indeed the compounds

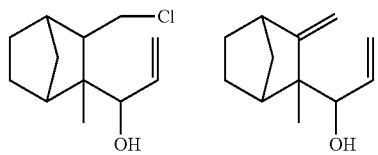

are disclosed as key intermediates in the synthesis of β-santalol.

Alternatively, Herbert et al. in Tetrahedron Letters, 1970, 41, report an alternative preparation of β-santalol involving a laborious sequence of double bond hydration/dehydration and bromination/debromination.

However, said approaches either require an expensive, or not easy to prepare industrially, starting material (e.g. Herbert et al.) or provide β-santalol with very low overall yields (e.g. U.S. Pat. No. 4,197,411, EP 10213). None of said prior art documents suggests the present invention's embodiments.

Therefore, in the industry, there is still a need for a more efficient process for the preparation of β-santalol and derivatives thereof. The aim of the present invention is to solve said need by providing a process which allows the preparation of the targeted compounds with improved overall yields, as well as diminished number of synthetic steps.

DESCRIPTION OF THE INVENTION

A first object of the present invention is a compound of formula

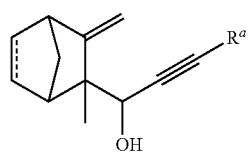
(I)

in the form of any one of its stereoisomers or mixtures thereof, and wherein the dotted line represents a carbon-carbon single or double bond, and $R^a$ represents a hydrogen atom or a $Si(R^b)_3$ or $(R^b)_2COH$ group, each $R^b$ representing $C_{1-6}$ alkyl group or a phenyl group.

Indeed, we have now found that β-santalol (an important perfuming ingredient), and derivatives thereof, can be advantageously prepared starting from a propargyl alcohol of formula (I) wherein $R^a$ is a hydrogen atom, or from the equivalent compound wherein the acetylene position is protected, wherein $R^a$ is not a hydrogen atom.

Said compound (I) can be obtained by various methods, as shown in the Examples. However we surprisingly found a process starting from the unknown intermediate (II) which allows higher yields. Therefore, a second object of the present invention concerns a process for the preparation of a compound (I), as defined above, comprising the following steps:
a) reacting a compound of formula

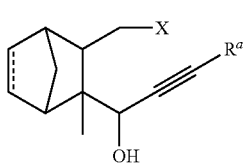
(II)

in the form of any one of its stereoisomers or mixtures thereof, and wherein the dotted line and $R^a$ have the same meaning as in formula (I), and X represents a halogen atom, a $C_{1-4}$ acyl group, a $C_{1-4}$ alkoxyl group, phenyl sulfonate optionally substituted by one or two $C_{1-3}$ alkyl groups such as tosylate, or a $C_{1-4}$ alkyl sulfonate such as mesylate, or a group of formula OC(=O)OR$^c$, wherein $R^c$ is a $C_1$-$C_7$ alkyl group;
with a base having a pK$_a$ above 16, preferably comprised between 16 and 30;
b) optionally, when $R^a$ is not a hydrogen atom, treating the compound obtained in step a) (methylene derivative resulting from the elimination of HX) with a suitable base or a fluorine salt to obtain compound (I) wherein $R^a$ is hydrogen atom.

According to any one of the embodiments of said aspect of the invention, said base of step a) is a $C_{1-6}$ alkaline alkoxide, such as sodium or potassium methoxide, ethoxide, iso-propoxide or ter-butoxide; a $C_{2-8}$ alkaline amide, such as LDA (lithium di-isopropyl amide); or a $C_{9-12}$ polycyclic amidine or diamine, such as DBU. In particular, said base is a $C_{3-6}$ alkaline alkoxilate such as sodium or potassium ter-butoxide, iso-propoxide or amyloxide.

The suitable bases or fluorine salt necessary for step b) are well known by a person skilled in the art. However one may cite, as non limiting examples, the following compounds: KOH, borax ($Na_2B_4O_7$), KF or $K_2CO_3$/18-C-6 ether.

The transformation of (II) into (I), in any of its embodiments and in particular for step a), is preferably carried out in the presence of solvent. Non-limiting examples of such a solvent are $C_{2-12}$ amides, in particular $C_{3-8}$ N-alkyl or N,N-dialkyl amide (e.g. acetamide, N,N-dimethyl-acetamide, N,N-dimethyl-formamide, N-acetyl piperidine or N-acetylpyrrolidine), $C_{2-6}$ sulphoxide (e.g. DMSO), $C_{6-9}$ N-alkyl lactame (e.g. N-methyl pyrrolidone) and mixtures thereof. More preferably, the solvent is DMF, DMSO, N-methylpyrrolidone and mixtures thereof.

The temperature, at which the transformation of (II) into (I) according to the invention can be carried out, in any of its embodiments and in particular for step a), is comprised between $-10°$ C. and $100°$ C., preferably between $0°$ C. and $80°$ C. Of course a person skilled in the art is also able to select the preferred temperature as a function of the melting and boiling point of the starting and final products and/or an eventual solvent.

The compound of formula (II), is also a novel compound and a further object of the present invention. Said compound (II) can be obtained according to a process comprising the following steps:

a') reacting a compound of formula

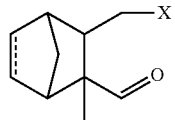

(III)

wherein the dotted line and X have the same meaning as indicated in formula (I); with a compound of formula $R^a$—C≡CY, wherein $R^a$ has the same meaning as in formula (I), and Y represents an alkaline metal or a MgZ or ZnZ group wherein Z is a halogen atom;

b') optionally, when $R^a$ is not a hydrogen atom, treating the obtained compound (methylene derivative resulting from the elimination of HX) with a suitable base or a fluorine salt to obtain compound (I) wherein $R^a$ is a hydrogen atom.

The compounds responding to formula (III) are known compounds and can be prepared according to the literature, e.g. see U.S. Pat. No. 4,197,411.

Step b') can be performed as above described for step b).

The transformation of (III) into (II), in any of its embodiments and in particular for step a'), is preferably carried out in the presence of solvent. Non-limiting examples of such a solvent are $C_{4-8}$ ethers or aromatic hydrocarbons and mixtures thereof. More preferably, the solvent is toluene or THF and mixtures thereof.

The temperature, at which the transformation of (III) into (II) according to the invention can be carried out, in any of its embodiments and in particular for step a'), is comprised between $-20°$ C. and $100°$ C., preferably between $-10°$ C. and $40°$ C. Of course a person skilled in the art is also able to select the preferred temperature as a function of the melting and boiling point of the starting and final products and/or an eventual solvent.

In particular, steps b) and b') are well known reaction and a person skilled in the art is able to apply its standard knowledge to perform them.

According to any one of the embodiments of said aspect of the invention, Z may represent a Cl, Br or I atom.

According to any one of the embodiments of said aspect of the invention, Y may represent Li, Na, MgCl, MgBr or MgI.

Examples of how to perform said processes are provided in the Examples part of the description.

As mentioned above, the propargyl alcohol (I) has been found to be a useful precursor of β-santalol; in particular compound (I) in which $R^a$ represents a hydrogen atom is a direct precursor of a key intermediate of β-santalol, and compounds (I) in which $R^a$ does not represent a hydrogen atom are direct precursors of compound (I) in which $R^a$ represent a hydrogen atom. Indeed propargyl (I), wherein $R^a$ is a hydrogen atom, can be used for the preparation of an aldehyde (IV), as defined below, which is known to be an important intermediate in the preparation of β-santalol and derivatives thereof.

Consequently, a further object of the present invention is a process for the preparation of a compound of formula

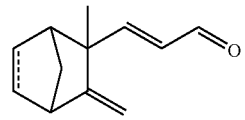

(IV)

in the form of any one of its stereoisomers or mixtures thereof, and wherein the dotted line has the same meaning as in formula (I);

by 1) reacting a compound (I-a)

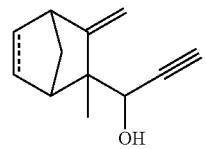

(I-a)

in the form of any one of its stereoisomers or mixtures thereof, wherein the dotted line has the same meaning as in formula (I);

with a complex selected amongst:

a vanadyl derivative of formula $[V_2O_6SiPh_2]_n$ or $(Ph_3SiO)_3$VO wherein Ph represents a phenyl group optionally substituted by one or two methyl groups, and n indicates that the compound is a monomeric, oligomeric or polymeric form;

a Ru complex of formula $[CpRuCl(PR_3)]$, wherein Cp indicates a cyclopentadienyl optionally substituted by one to five $C_{1-2}$ alkyl groups, and R represents $C_{1-5}$ alkyl groups or a phenyl group optionally substituted by one or two methyl, methoxy or CF$_3$ groups; or mixture of a cuprous halide, such as CuBr or CuCl, a Ti(OR)$_4$ salt wherein R is as defined above, such as Ti(O$^i$Pr)$_4$ or (Ti(O"Bu)$_4$, and a C$_{1-10}$ carboxylic acid, such as p-toluic acid 2) optionally hydrogenating the compound of formula

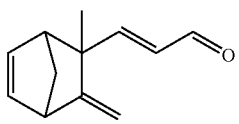
(IV')

in the form of any one of its stereoisomers or mixtures thereof;

(obtained in step 1 if the dotted line of compound (I-a) represents a double bond) into a compound of formula

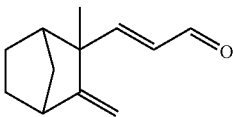
(IV'')

in the form of any one of its stereoisomers or mixtures thereof.

Step 1) is a Meyer-Schuster rearrangement and is a well known general reaction in the art. According to a particular embodiment, said complex of step 1) is:

a vanadyl derivative of formula [V$_2$O$_6$SiPh$_2$]$_n$ or (Ph$_3$SiO)$_3$VO wherein Ph represents a phenyl group, and n indicates that the compound is a polymeric form (see L. A. Kheifits et al., *Tetrahedron Letters* 1976, 17, 2981; H. Pauling et al. *Helv. Chim. Acta* 1976, 59, 1233; K. Takai et al. *Tetrahedron Letters* 1985, 26, 5585);

a Ru complex of formula [CpRuCl(PMe$_3$)], wherein Cp indicates a cyclopentadienyl (see T. Suzuki, M. Tokunaga, Y. Wakatsuki, *Tetrahedron Letters* 2002, 43, 7531); or mixture of a CuCl, (Ti(O"Bu)$_4$, and p-toluic acid (see R. K. Boeckman Jr et al. *Helv. Chim. Acta* 2002, 85, 4532).

The transformation of (I-a) into (IV), in any of its embodiments and in particular for step 1), is preferably carried out in the presence of solvent. Non-limiting examples of such a solvent are water and C$_{3-6}$ alcohols mixtures or aromatic hydrocarbons. More preferably, the solvent is a mixture of water and $^i$PrOH or toluene or xylene.

The temperature, at which the transformation of (I-a) into (IV) according to the invention can be carried out, in any of its embodiments and in particular for step 1), is comprised between about 80° C. and about 160° C., preferably between about 100° C. and about 150° C. Of course a person skilled in the art is also able to select the preferred temperature as a function of the melting and boiling point of the starting and final products and/or an eventual solvent.

Said complex in step 1) can be added to the reaction medium in a large range of concentrations. As non-limiting examples, one can cite salt concentrations ranging from 0.01 to 0.20 molar equivalents, relative to the molar amount of the starting compound (I-a) alcohol (I). Preferably, the complex concentration will be comprised between 0.03 and 0.10 molar equivalents. It goes without saying that the optimum concentration of the complex will depend on the nature of the latter and on the desired reaction time.

Step 2 can be performed using standard hydrogenation conditions, which are well known by a person skilled in the art. In particular it can be used a hydrogenation catalyst such as Ni(P2) (NaBH$_4$, Ni(OAc)$_2$, H$_2$, EtOH, W. Oppolzer, C. Chapuis, *Tetrahedron Letters* 1983, 24, 4665) or Lindlar, (C. Fehr, I. Magpantay, J. Arpagaus, X. Marquet, M. Vuagnoux, *Angew. Chem. Intl. Ed.* 2009, 48, 7221).

The transformation of (IV') into (IV''), in any of its embodiments and in particular for step 2), is preferably carried out in the presence of solvent. Non-limiting examples of such a solvent are mixtures of a C$_{1-4}$ alkyl alcohol, such as EtOH, and H$_2$O.

The temperature, at which the transformation of (IV') into (IV'') can be performed, in any of its embodiments and in particular for step 2), is comprised between about 0° C. and about 50° C., preferably between about 0° C. and about 20° C. Of course a person skilled in the art is also able to select the preferred temperature as a function of the melting and boiling point of the starting and final products and/or an eventual solvent.

The H$_2$ pressure, at which the transformation of (IV') into (IV'') can be performed, in any of its embodiments and in particular for step 2), is comprised between about 1 bar and about 10 bars, preferably between about 1 bar and about 5 bars. Of course a person skilled in the art is also able to select the preferred temperature as a function of the melting and boiling point of the starting and final products and/or an eventual solvent.

Examples of how to perform said processes are provided in the Example part of the description.

According to any embodiment of the invention, and independently of the specific aspects, the compounds (I), (I-a), (II), (III) or (IV) can be in the form of any one of its stereoisomers or mixtures thereof. By the term stereoisomer it is intended any diastereomer, enantiomer, racemate or carbon-carbon isomer of configuration E or Z.

According to any one of the above embodiments of the invention, said compounds (I), (I-a), (II), (III) or (IV) are each in the form of a mixture of stereoisomers comprising more than 50% (w/w) of:

the (1RS,4SR) or the (1RS,2SR,4SR) diastereoisomer, when the dotted line represents a single bond; or the (1RS,4SR) or the (1RS,2RS,4SR) diastereoisomer, when the dotted line represents a double bond;

i.e. a compound having the relative configurations as shown in the formulae

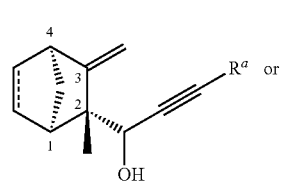
(I-b)

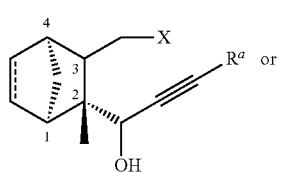
(II-b)

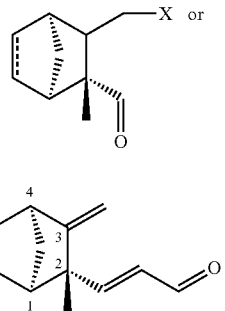 (III-b)

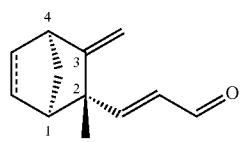 (IV-b)

and in a further embodiment said compounds consist essentially in the compound (I), (I-a), (II), (III) or (IV) each in the form of a mixture of stereoisomers comprising more than 70%, or 80% or 90%, (w/w) of the (1RS,4SR), or of the (1RS,2SR,4SR), or of the (1RS,2RS,4SR), diastereoisomer.

According to any one of the above embodiments of the invention, said compounds are each in the form of a mixture of stereoisomers comprising more than 50% (w/w) of:

the (1S,4R) or (1S,2R,4R) enantiomer, when the dotted line represents a single bond; or the (1R,4S) or (1R,2R,4S) enantiomer, when the dotted line represents a double bond;

i.e. a compound having the absolute configuration as shown in the formulae

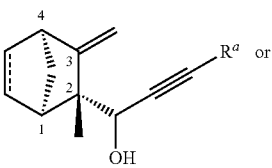 (I-c)

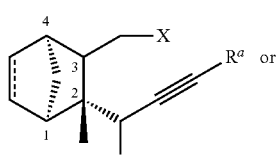 (II-c)

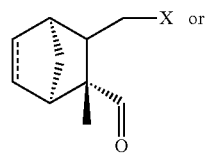 (III-c)

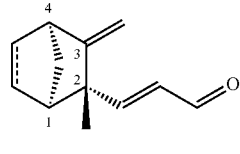 (IV-c)

and in a further embodiment said compounds consist essentially in the compound (I), (I-a), (II), (III) or (IV) each in the form of a mixture of stereoisomers comprising more than 70%, or 80% or 90%, (w/w) of the above specified stereoisomer.

As typical examples of compounds (I), one may cite 1-((1RS,2SR,4SR)-2-methyl-3-methylenebicyclo[2.2.1]heptan-2-yl)prop-2-yn-1-ol, 1-((1S,2R,4R)-2-methyl-3-methylenebicyclo[2.2.1]heptan-2-yl)prop-2-yn-1-ol, (1RS, 2RS,4SR)-2-methyl-3-methylenebicyclo[2.2.1]hept-5-en-2-yl)prop-2-yn-1-ol or (1R,2R,4S)-2-methyl-3-methylenebicyclo[2.2.1]hept-5-en-2-yl)prop-2-yn-1-ol As typical examples of compounds (II), one may cite (1RS, 2SR,3SR,4SR)-3-(chloromethyl)-2-methylbicyclo[2.2.1]heptan-2-yl)prop-2-yn-1-ol, (1S,2R,3R,4R)-3-(chloromethyl)-2-methylbicyclo[2.2.1]heptan-2-yl)prop-2-yn-1-ol, (1RS,2 SR,3 SR,4SR)-3-(bromomethyl)-2-methylbicyclo[2.2.1]heptan-2-yl)prop-2-yn-1-ol, (1S,2R,3R,4R)-3-(bromomethyl)-2-methylbicyclo[2.2.1]heptan-2-yl)prop-2-yn-1-ol, (1RS,2RS,3RS,4SR)-3-(chloromethyl)-2-methylbicyclo[2.2.1]hept-5-en-2-yl)prop-2-yn-1-ol, (1R,2R,3R,4S)-3-(chloromethyl)-2-methylbicyclo[2.2.1]hept-5-en-2-yl)prop-2-yn-1-ol, (1RS,2RS,3RS,4SR)-3-(bromoomethyl)-2-methylbicyclo[2.2.1]hept-5-en-2-yl) prop-2-yn-1-ol or (1R,2R,3R,4S)-3-(bromoomethyl)-2-methylbicyclo[2.2.1]hept-5-en-2-yl)prop-2-yn-1-ol.

As typical examples of compounds (III), one may cite (1RS,2SR,3SR,4SR)-3-chloro methyl-2-methylbicyclo[2.2.1]heptane-2-carbaldehyde, (1S,2R,3R,4R)-3-chloro methyl-2-methylbicyclo[2.2.1]heptane-2-carbaldehyde, (1RS,2SR,3SR,4SR)-3-bromo methyl-2-methylbicyclo[2.2.1]heptane-2-carbaldehyde, (1S,2R,3R,4R)-3-bromo methyl-2-methylbicyclo[2.2.1]heptane-2-carbaldehyde, (1RS,2RS,3RS,4SR)-3-(Chloromethyl)-2-methylbicyclo[2.2.1]hept-5-ene-2-carbaldehyde, (1R,2R,3R,4S)-3-(Chloromethyl)-2-methylbicyclo[2.2.1]hept-5-ene-2-carbaldehyde, (1RS,2RS,3RS,4SR)-3-(bromomethyl)-2-methylbicyclo[2.2.1]hept-5-ene-2-carbaldehyde or (1R,2R,3R,4S)-3-(bromomethyl)-2-methylbicyclo[2.2.1]hept-5-ene-2-carbaldehyde.

As typical examples of compounds (IV), one may cite (E or Z)-3-((1SR,2SR,4RS)-2-methyl-3-methylenebicyclo[2.2.1]heptan-2-yl)acrylaldehyde, (E or Z)-3-((1S,2S,4R)-2-methyl-3-methylenebicyclo[2.2.1]heptan-2-yl)acrylaldehyde, (E or Z)-3-((1RS,2SR,4SR)-2-methyl-3-methylenebicyclo[2.2.1]hept-5-en-2-yl)acrylaldehyde or (E or Z)-3-((1R,2S,4S)-2-methyl-3-methylenebicyclo[2.2.1]hept-5-en-2-yl) acrylaldehyde.

According to any one of the above embodiments of the invention, X may represent a halogen atom, such as a Cl or Br atom or a sulfonate group as defined above. In particular said X may represent a Cl or Br atom.

According to any one of the above embodiments of the invention, $R^a$ may represents a hydrogen atom or a $Si(R^b)_3$, each $R^b$ representing $C_{1-4}$ alkyl group or a phenyl group. In particular, said $R^a$ represents a hydrogen atom.

For the sake of clarity, by the expression "wherein the dotted line represents a carbon-carbon single or double bond", or the similar, it is meant the normal meaning understood by a person skilled in the art, i.e. that the whole bonding (solid and dotted lines) between the carbon atoms connected by said dotted line, e.g. carbon 5 and 6, is a carbon-carbon single or double bond.

As mentioned above, the invention's compounds are useful intermediates for the preparation of important perfuming ingredient such as β-santalol.

Non-limiting examples of how to perform the preparation of β-santalol or a derivative thereof, from the compounds of formula (I) are provided in the Examples part of the description. However we can summarize such approach as follows:

i) preparing a compound (I), e.g. from compound (II) as described above;

ii) converting compound (I) in compound (IV') or (IV''), e.g. as described above;
iii) converting compound (IV'') into β-santalol.

Steps i) and ii) are described above. Step iii) can be performed as described in the literature, e.g. in U.S. Pat. No. 4,197,411, by Hoffmann et al, in J. Lieb. Ann. Chem, 1979, 743, or in WO 2009/141781. Practical examples of step iii) are provided in the Examples herein below.

However, as non-limiting example, one of the most direct manners to transform the aldehyde (IV'') into β-santalol comprises the following reactions:

A. reducing (hydrogenation) the aldehyde (IV') or (IV'') into and aldehyde of formula (V)

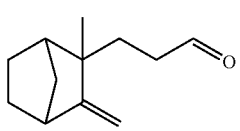

(V)

in the form of any one of its stereoisomers or mixtures thereof;

B. coupling said aldehyde (V) with an aldehyde MeCH$_2$CHO (Aldol addition) to obtain an aldehyde (VI)

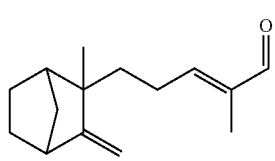

(VI)

in the form of any one of its stereoisomers or mixtures thereof;

C. converting said compound (VI) into the corresponding dienol derivative (VII)

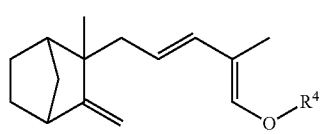

(VII)

in the form of any one of its stereoisomers or mixtures thereof, and wherein R$^4$ represents a C$_1$-C$_3$ acyl group or a C$_3$-C$_8$ silyl group;

D. reducing the enolate (VII) into a compound (VIII)

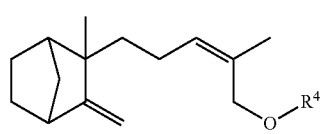

(VIII)

in the form of any one of its stereoisomers or mixtures thereof, and wherein R$^4$ has the same meaning as in formula (VI), and converting compound (VIII) into β-santalol.

According to a particular embodiment of the invention, said compounds (V) to (VIII) possess a configuration corresponding to the one described above for compounds (I) or (II).

Steps A) to D) can be performed according to standard methods well known by a person skilled in the art. For instance, the hydrogenation of step A) can be performed with Ni-Raney as catalyst.

For instance, one may cite the following method for each step:
step A) or B) according to EP 10213;
step C) according to Simmons et al. in Helv. Chim. Acta, 1988, 71, 1000, or WO 2005/037243; and
step D) according to Shibasaki et al., in J. Org. Chem., 1988, 53, 1227 (where is reported the [1,4] hydrogenation of a dienol acetate derivative) or according to WO 08/120,175.

EXAMPLES

The invention, in all its embodiments, will now be described in further detail by way of the following examples, wherein the abbreviations have the usual meaning in the art, the temperatures are indicated in degrees centigrade (° C.); the NMR spectral data were recorded in CDCl$_3$ with a 400 MHz or 125 MHz machine for $^1$H or $^{13}$C respectively, the chemical shifts δ are indicated in ppm with respect to TMS as standard, the coupling constants J are expressed in Hz.

Starting compound (III): (1RS,2RS,3RS,4SR)-3-(Chloromethyl)-2-methylbicyclo[2.2.1]hept-5-ene-2-carbaldehyde (X=Cl) 12a and (1RS,2RS,3RS,4SR)-3-(acetatemethyl)-2-methylbicyclo[2.2.1]hept-5-ene-2-carbaldehyde (X=OAc) 12c as well as (1RS,2SR,3SR,4SR)-3-chloromethyl-2-methylbicyclo[2.2.1]heptane-2-carbaldehyde (X=Cl) 13a and ((1RS,2SR,3SR,4SR)-2-formyl-2-methylbicyclo[2.2.1]heptan-3-yl)methyl acetate (X=OAc) 13c. were obtained according to the literature (see U.S. Pat. No. 4,197, 411 and M. Baumann, W. Hoffmann, Liebigs Ann. Chem. 1979, 743.).

Other compounds of formula (III) were obtained as follows (see Scheme 1):

Scheme 1:

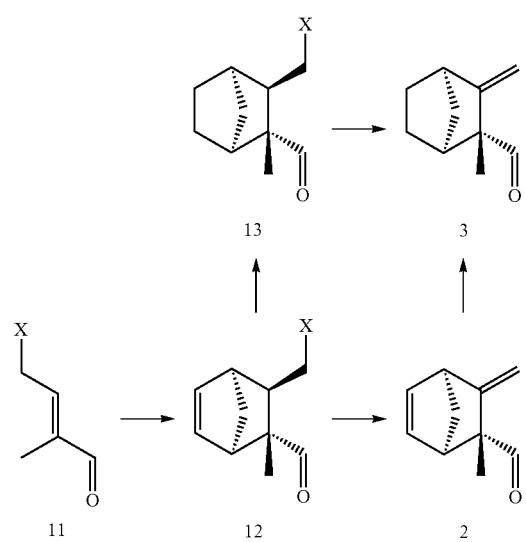

wherein the letter following the number (see below) has the meaning: a: X=Cl; b: X=Br; c: X=OAc; d: X=OH; e: X=OTs; f: X=OMs;

(1RS,2RS,3RS,4SR)-3-(Bromomethyl)-2-methylbicyclo[2.2.1]hept-5-ene-2-carbaldehyde 12b (X=Br)

In a 250 ml round bottomed 4 necked flask equipped with a mechanic stirrer, a digital thermometer and a water refrigerant under Argon, were added CH$_2$Cl$_2$ (50 ml), the BF$_3$.O.Et$_2$O (0.478 ml, 1.94 mmol). Then a solution of cyclopentadiene (3.59 g, 54.3 mmol) and the bromo aldehyde 11b (7.9 g, 38.8 mmol) in CH$_2$Cl$_2$ (15 ml) was added dropwise in 45 min at −20°. The solution was stirred at −20° for 30 minutes. After entire consumption of the starting material, the brown solution was poured onto ice (300 g) and extracted with Et$_2$O. The organic layer was washed with a 10% solution of NaHCO$_3$, then with brine, and the organic phase was dried over Na$_2$SO$_4$, filtered and evaporated to afford 9.2 g of a brown viscous oil. A bulb to bulb distillation afforded 12b as a 5:95 endo/exo mixture in 70% yield.

$^1$H-NMR: 9.61 (s, 1H); 6.38-6.29 (m, 2H); 3.18 (dd, J=6, 9, 1H); 3.15 (brs, 1H); 2.99 (m, 2H); 2.95 (brs, 1H); 1.42 (tq, J=2, 9, 2H); 0.95 (s, 3H).

$^{13}$C-NMR: 203.8 (d); 136.9 (d); 136.2 (d); 57.5 (s); 50.7 (d); 47.2 (d); 46.0 (t); 45.4 (d); 34.2 (t); 14.8 (q).

((1RS,2SR,3SR,4SR)-3-bromo methyl-2-methylbicyclo[2.2.1]heptane-2-carbaldehyde 13b (X=Br)

A suspension of 10% Pd/C (300 mg) in AcOEt (250 ml) and 12b (6.6 g, 14.12 mmol) was hydrogenated for 15.5 hours (535 ml of H$_2$ consumed). The suspension was filtered over Celite, dried and concentrated to obtain 6.4 g of a yellow oil. A bulb to bulb distillation 90°/0.09 mbar gave 13b in 95% yield.

$^1$H-NMR: 9.43 (s, 1H); 3.38 (d, J=2.5, 1H); 3.36 (s, 1H); 2.73 (ddt, J=2, 4, 9, 1H); 2.51 (brs, 1H); 2.35 (brd, J=2, 1H); 1.66-1.60 (m, 1H); 1.51-1.24 (m, 5H); 1.05 (s, 3H).

$^{13}$C-NMR: 203.4 (d); 53.7 (s); 44.2 (d); 43.7 (d); 41.2 (d); 36.5 (t); 31.8 (t); 23.0 (t); 21.0 (t); 12.5 (q).

(1RS,2SR,3SR,4SR)-3-(hydroxymethyl)-2-methylbicyclo[2.2.1]heptane-2-carbaldehyde 13d (X=OH)

A 3 necked 50 ml round bottomed flask equipped with a magnetic stirrer, water refrigerant, under N$_2$ was charged with KOH (628 mg, 9.51 mmol) and H$_2$O (1.714 ml, 95 mmol), MeOH (15 ml) and the acetate 13c (500 mg, 2.38 mmol). The reaction mixture was heated to reflux until full conversion (15 minutes), then the reaction was cooled down and poured onto an ice cold 10% H$_2$SO$_4$ solution and extracted with Et$_2$O. The organic layer was washed with saturated NaHCO$_3$, brine, and dried over Na$_2$SO$_4$, then filtered and concentrated to 338 mg of a crude yellow oil. A bulb to bulb distillation (130°/2 mbar) afforded pure 13d in 98% yield.

$^1$H-NMR: 9.44 (s, 1H); 3.68-3.59 (m, 2H); 2.38 (brs, 1H); 2.29 (brs, 1H); 1.82 (brs, 1 OH); 1.66-1.60 (m, 1H); 1.50-1.25 (m, 6H); 1.05 (s, 3H).

$^{13}$C-NMR: 204.8 (d); 60.6 (t); 52.9 (s); 43.9 (d); 43.7 (d); 39.4 (d); 37.2 (t); 23.1 (t); 21.7 (t); 12.5 (q).

(1RS,2SR,3SR,4SR)-3-(methyltoluenesulfonate)-2-methylbicyclo[2.2.1]heptane-2-carbaldehyde 13e (X=OTs)

A 3 necked 50 ml round bottomed flask equipped with a magnetic stirrer, water refrigerant, under N$_2$ was charged with alcohol 13d (400 mg, 2.38 mmol) and pyridine (15 ml). The solution was then cooled to 0° and pTsCl (453 mg, 2.38 mmol) was added portionwise. The reaction was stirred at 20° overnight until full conversion. The reaction mixture was then poured onto an ice cold 10% H$_2$SO$_4$ solution and extracted with Et$_2$O, the organic layer was washed with saturated NaHCO$_3$, brine, then dried over Na$_2$SO$_4$, filtered and evaporated to afford 910 mg of the crude product. Purification over a 25 g SiO$_2$ cartridge with cyclohexane/AcOEt 85:15 afforded pure tosylate 13e in 53% yield.

$^1$H-NMR: 9.37 (s, 1H); 7.80 (d, J=16, 2H); 7.37 (d, J=16, 2H); 4.10-3.97 (m, 2H); 2.59 (dt, J=4, 10, 1H); 2.49 (s, 3H); 2.35 (brs, 1H); 2.26 (brd, J=3, 1H); 1.63-1.52 (m, 1H); 1.42 (s, 3H); 1.34-1.24 (m, 2H); 0.99 (s, 3H).

$^{13}$C-NMR: 203.0 (d); 144.8 (s); 133.0 (s); 129.9 (2d); 127.9 (2d); 68.6 (t); 52.8 (s); 43.6 (d); 39.7 (d); 39.5 (d); 36.8 (t); 22.8 (t); 21.7 (q); 21.6 (t); 12.6 (q).

(1RS,2SR,3SR,4SR)-3-(methylmethylsulfonate)-2-methylbicyclo[2.2.1]heptane-2-carbaldehyde 13f (X=OMs)

A 3 necked 50 ml round bottomed flask equipped with a magnetic stirrer, water refrigerant, under N$_2$ was charged with alcohol 13d (500 mg, 2.97 mmol), CH$_2$Cl$_2$ (15 ml), and Et$_3$N (451 mg, 4.46 mmol), the solution was then cooled to 0° and MeSO$_2$Cl (392 mg, 3.42 mmol) was added dropwise. The reaction mixture was stirred at 0° for 30 minutes—full conversion and then poured onto an ice cold 5% HCl solution, and extracted with Et$_2$O. The organic layer was washed with H$_2$O, saturated NaHCO$_3$, brine and dried over Na$_2$SO$_4$, then filtered and concentrated to afford 740 mg of the crude product. Purification on a 25 g SiO$_2$ cartridge with cyclohexane/AcOEt 85/15 afforded mesylate 13f in 40% yield.

$^1$H-NMR: 9.42 (s, 1H); 4.30-4.16 (m, 2H); 3.00 (s, 3H); 2.71 (dt, J=3, 10, 1H); 2.42 (brs, 1H); 2.30 (brd, J=3, 1H); 1.68-1.64 (m, 1H); 1.53-1.25 (m, 5H); 1.07 (s, 3H).

$^{13}$C-NMR: 203.0 (d); 68.0 (t); 53.0 (s); 43.7 (d); 39.7 (d); 39.6 (d); 37.6 (q); 36.9 (t); 22.8 (t); 21.8 (t); 12.7 (q).

(1RS,2RS,4SR)-2-methyl-3-methylenebicyclo[2.2.1]hept-5-ene-2-carbaldehyde 2

Obtained in 60% yield from 12b according to the DBU elimination procedure used for 3.

$^1$H-NMR: 9.67 (s, 1H); 6.28 (m, 1H); 6.21 (m, 1H); 5.17 (s, 1H); 4.77 (s, 1H); 3.28 (s, 1H); 3.04 (s, 1H); 1.73 (m, 1H); 1.66 (m, 1H); 1.10 (s, 3H).

$^{13}$C-NMR: 203.1 (d); 152.9 (s); 137.7 (d); 135.4 (d); 106.8 (t); 58.3 (s); 51.5 (d); 48.7 (d); 47.9 (t); 21.0 (q).

(1RS,2SR,4SR)-2-methyl-3-methylenebicyclo[2.2.1]heptane-2-carbaldehyde 3

A 1M soln. of NaBH$_4$ (0.36 ml, 0.36 mmol) in EtOH was added to a suspension of Ni(OAc)$_2$ (89 mg, 0.36 mmol) in EtOH (1.3 ml) under H$_2$. After 30 min, a soln. of 2 (424 mg, 2.86 mmol) in EtOH/H$_2$O 9:1 (1 ml) was added. The mixture was stirred at 20° under 1 atm of H$_2$, until absorption of 1.0 mol.-equiv. of H$_2$. Filtration, then concentration of the reaction mixture afforded pure 3 in 95% yield. Also obtained in 53% yield from 13b (X=Br) or 13e (X=OTs), or 73% yield from 13f (X=OMs) according to the following DBU elimination procedure: To a 3 necked 100 ml round bottomed flask equipped with a magnetic stirrer, a thermometer and a water refrigerant under Ar, were added 13 (bromide, or tosylate or mesylate 1.613 mmol), DMF (10 ml). NaI (242 mg, 1.613 mmol) and DBU (614 mg, 4.03 mmol). The mixture was stirred at 80° for 50 hrs. The reaction was cooled to 20° and poured onto 2% aq. HCl, then extracted with Et$_2$O, after washing with brine, the organic layer was dried over Na$_2$SO$_4$, filtered and evaporated to obtain an oil. A purification over a 12 g SiO$_2$ cartridge with cyclohexane/AcOEt 95:5 afforded 3.

$^1$H-NMR: 9.40 (s, 1H); 5.05 (s, 1H); 4.66 (s, 1H); 2.77 (brd, J=4.7, 1H); 2.52 (brd J=3.2, 1H); 1.74 (m, 2H); 1.67 (m, 1H); 1.54 (m, 1H); 1.35 (m, 2H); 1.17 (s, 3H).

$^{13}$C-NMR: 201.9 (d); 156.7 (s); 104.5 (t); 57.9 (s); 45.8 (d); 42.7 (d); 37.6 (t); 29.8 (t); 22.9 (t); 18.2 (q).

Example 1

Preparation of a Compound (I)

Scheme 2:

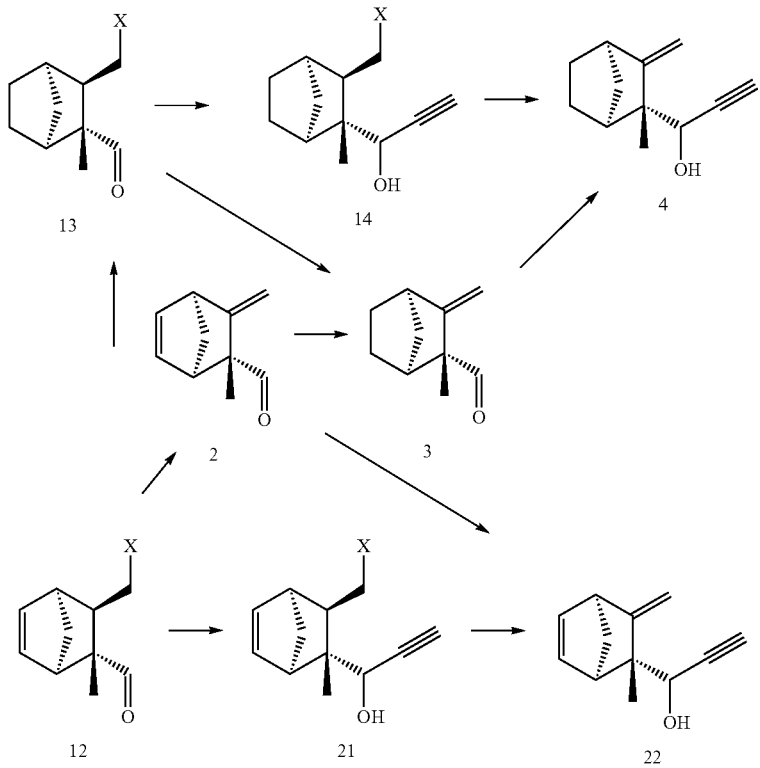

Compounds (II) with the Dotted Line Representing a C—C

((1RS,2SR,3SR,4SR)-3-(chloromethyl)-2-methylbicyclo[2.2.1]heptan-2-yl)prop-2-yn-1-ol 14a A solution of chloraldehyde 13a (0.5 g, 2.53 mmol) in THF (5 ml) was added dropwise at 0° C. to a solution of ethynylmagnesium bromide in THF (0.5M, 10 ml, mmol). After the addition was completed (5 min), the solution was poured onto saturated $NH_4Cl$, washed with brine, dried, and evaporated under vaccuo at <40° C. to obtain 470 mg of an oil. Purification over a 12 g $SiO_2$ cartridge with cyclohexane/AcOEt 95/5 furnished 14a in 68% yield.

$^1$H-NMR: 4.20 (brd, J=3.3, 1H); 3.66 (dd, J=4.6, 10.6, 1H); 3.54 (dd, J=11.1, 12.4, 1H); 2.49 (brs, 1H); 2.42 (d, J=2.8, 1H); 2.32 (brs, 1H); 2.05 (brd, J=5.7, 1H); 1.79 (dt, J=4.3, 12.1, 1H); 1.56 (m, 2H); 1.42 (m, 3H); 1.27 (m, 1H); 0.95 (s, 3H).
$^{13}$C-NMR: 83.4 (s); 73.3 (d); 69.1 (d); 48.8 (d); 46.3 (s); 44.1 (d); 43.4 (t); 39.4 (d); 36.0 (t); 24.5 (t); 20.2 (t); 12.0 (q).

((1R,2SR,3SR,4SR)-3-(bromomethyl)-2-methylbicyclo[2.2.1]heptane-2-yl)prop-2-yn-1-ol 14b Obtained in 66% yield from 13b as a 4:1 mixture of stereoisomers according to the procedure used for 14a.

$^1$H-NMR: isomer A 4.19 (s, 1H); 3.55 (dd, J=4.2, 10, 1H); 3.42 (dd, J=9.2, 11.7. 1H); 2.51 (brs, 1H); 2.42 (d, J=2.5, 1H); 2.39 (brs, 1H); 1.99 (brs, 10H); 1.86 (dt, J=3.3, 11.7, 1H); 1.56 (dt, J=3.3, 11.7, 2H); 1.43-1.25 (m, 4H); 0.95 (s, 3H);
isomer B 4.24 (s, 1H); 3.51 (dd, J=4.3, 9.3, 1H); 3.41 (dd, J=9.9, 11.2, 1H); 2.52 (brs, 1H); 2.47, (d, J=2.5, 1H); 2.25 (brs, 1H); 2.15 (dt, J=4.3, 11.2, 1H); 2.00 (brs, 10H); 1.65-1.60 (m, 2H); 1.41-1.35 (m, 3H); 1.29-1.25 (m, 2H); 0.96 (s, 3H).
$^{13}$C-NMR: isomer A 83.3 (s); 73.2 (d); 69.1 (d); 48.8 (d); 46.9 (s); 44.3 (d); 40.2 (d); 35.9 (t); 32.6 (t); 24.4 (t); 20.0 (t); 12.0 (q).
isomer B 83.2 (s); 74.3 (d); 70.3 (d); 49.6 (d); 47.1 (s); 45.7 (d); 41.0 (d); 36.5 (t); 33.4 (t); 24.5 (t); 20.0 (t); 12.0 (q).

Compounds (I) with the Dotted Line Representing a C—C

1-((1RS,2SR,4SR)-2-methyl-3-methylenebicyclo[2.2.1]heptan-2-yl)prop-2-yn-1-ol 4

A solution of alcohol 14a (21.8 mmol) in DMSO (150 ml) was added portionwise t-BuOK (4.9 g, 43.7 mmol) at room temperature. After the addition was complete, an exothermal (T=39°) was observed and the reaction temperature was left to reach room temperature for about 30 minutes. The cold solution was then poured onto saturated $NH_4Cl$, washed with $H_2O$, brine, extracted with $Et_2O$. The organic phase was dried ($Na_2SO_4$), filtered and evaporated to afford 4 in 78% yield.

$^1$H-NMR: 4.91 (s, 1H); 4.76 (s, 1H); 4.29 (m, 114); 2.73 (brd, J=3.5, 1H); 2.45 (d, J=1.8, 1H); 2.33 (brd, J=3.6, 1H); 2.23 (d, J=4.3, 1H); 1.73 (m, 3H); 1.47 (m, 2H); 1.29 (m, 1H); 1.22 (s, 3H).
$^{13}$C-NMR: 161.5 (s); 103.9 (t); 82.9 (s); 73.7 (d); 66.5 (d); 50.0 (s); 47.2 (d); 45.3 (d); 36.7 (t); 30.5 (t); 23.5 (t); 16.8 (q).

Alternatively, 4 was also obtained in 60% yield from 14b using the DBU elimination described for 3.
Alternatively, 4 was also obtained in 52% yield from 3, using the ethynyl addition procedure described for 14a.

Compounds (II) with the Dotted Line Representing a C≡C ((1RS,2RS,3RS,4SR)-3-(chloromethyl)-2-methylbicyclo[2.2.1]hept-5-en-2-yl)prop-2-yn-1-ol 21a Obtained in 79% yield from 12a, according to the above ethynyl addition procedure used for 14a.
$^1$H-NMR: 6.29 (dd, J=4, 7.8, 1H); 6.24 (dd, J=4, 7.8, 1H); 4.34 (d, J=3.5, 1H); 3.53 (dd, J=4, 7.8, 1H); 3.12 (brs, 1H); 3.03 (dd, J=7.8, 8.4, 1H); 2.90 (brs, 1H); 2.51 (d, J=1.8, 1H); 2.14 (brs, 10H); 2.07 (dt, J=4, 7.8, 1H); 1.59 (d, J=8.4, 1H); 1.49 (d, J=8.4, 1H); 0.89 (s, 3H).
$^{13}$C-NMR: 138.9 (d); 134.7 (d); 83.7 (s); 74.0 (d); 69.5 (d); 50.4 (s); 49.4 (d); 49.0 (d); 46.9 (t); 45.5 (d); 45.2 (t); 13.3 (q).

((1RS,2RS,3RS,4SR)-3-(bromomethyl)-2-methylbicyclo[2.2.1]hept-5-en-2-yl)prop-2-yn-1-ol 21b Obtained in 91% yield from 12b according to the ethynyl addition procedure used for 14a.
$^1$H-NMR: 6.31-6.24 (m, 2H); 4.33 (dd, J=2.2, 6.0, 1H); 3.45 (dd, J=4.6, 10.3, 1H); 3.15 (brs, 1H); 2.97 (brs, 1H); 2.92 (dd, J=8.5, 12.4, 1H); 2.52 (d, J=2.5, 1H); 2.15 (dt, J=5.2, 10.3, 1H); 2.08 (d, J=6.6, 1H); 1.60 (d, J=6.6, 1H); 1.47 (d, J=6.6, 1H); 0.89 (s, 3H).
$^{13}$C-NMR: 139.0 (d); 134.6 (d); 83.7 (s); 74.1 (d); 69.5 (d); 51.4 (s); 49.7 (d); 49.1 (d); 46.3 (d); 45.1 (t); 36.2 (t); 13.3 (q).

Compounds (I) with the Dotted Line Representing a C≡C ((1RS,2RS,4SR)-2-methyl-3-methylenebicyclo[2.2.1]hept-5-en-2-yl)prop-2-yn-1-ol 22

One Pot Addition/Elimination:

A solution of chloraldehyde 12a (7.9 g, 27.8 mmol) in THF (50 ml) was added dropwise at 0° C. over 30 minutes to a solution of ethynylmagnesium bromide in THF (0.5M, 86.8 ml, 43.4 mmol. After the addition was completed, the mixture was allowed to warm to 20° C. over a period of 2.5 hours. The solution was cooled down again to 0° C., and DMSO (250 ml) was added dropwise (maintaining the temperature at 5° C.) following by an addition of tBuOK (11.24 g, 100.2 mmol). The reaction temperature was left to reach room temp, and stirred at 20° C. for 3 hours (brownish suspension). The suspension was poured onto saturated NH$_4$Cl, washed with H$_2$O, brine, extraction was done with Et$_2$O, which was dried then over Na$_2$SO$_4$, filtered and evaporated to obtain 8.6 g of an oil. Purification through a 100 g SiO$_2$ cartridge with cyclohexane/AcOEt 95:5 afforded 22 in 67% yield.

Simple Elimination:

To a solution of 21a (4.6 g. 21.8 mmol) in DMSO (150 ml) was added portionwise t-BuOK (4.9 g, 43.7 mmol) at room temperature. After the addition was complete, an exothermal (T=39.2°) was observed and the reaction temperature was left to reach room temperature for about 30 min. The cold solution was then poured onto saturated NH$_4$Cl, washed with H$_2$O, brine, extracted with Et$_2$O. The organic phase was dried (Na$_2$SO$_4$), filtered and evaporated to afford 22 in 84% yield.
$^1$H-NMR: 6.19 (t, J=1.8, 2H); 5.08 (s, 1H); 5.00 (s, 1H); 4.43 (brs, 1H); 3.21 (brs, 1H); 3.08 (brs, 1H); 2.56 (d, J=2.1, 1H); 2.06 (brs, 1H); 1.88 (brd, J=8.8, 1H); 1.54 (brd, J=8.8, 1H); 1.13 (s, 3H).
$^{13}$C-NMR: 155.2 (s); 136.8 (d); 136.8 (d); 106.3 (t); 83.8 (s); 74.8 (d); 68.8 (d); 52.5 (d); 49.8 (s); 48.4 (d); 47.1 (t); 21.2 (q).

Alternatively, 22 was also obtained in 57% yield from 2 by addition of ethynyl MgBr, according to the procedure used for 14a.

Alternatively, 22 was also obtained in 77% yield from 21b according to the DBU elimination used for 3.

To summarize, 4 can be obtained with the following yields from 13:
Route: 13→14→4: 53% (X=Cl) or 40% (X=Br) (according to the invention)
Route: 13→3→4: 27% (X=Br)
To summarize 22 can be obtained with the following yields from 12:
Route: 12→21→22: 66% (X=Cl) or 70% (X=Br) (according to the invention)
Route: 12→2→22: 34% (X=Br)
Other Compounds:

Scheme 2a:

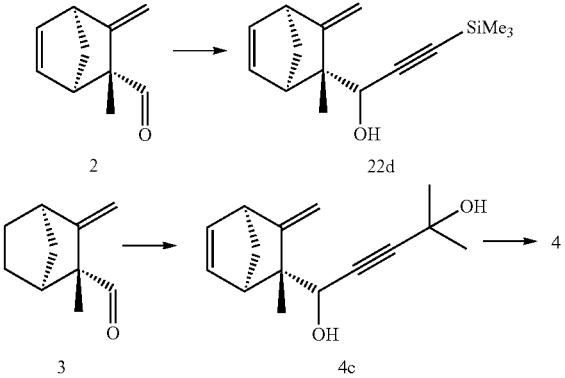

General Procedure for Addition of Mono-Protected:

A solution of nBuLi (1.6M/hexane, 1.3 mol.-equiv. for ethynyltrimethyl silane (–78° C.), or 2.5 mol.-equiv. for 2-methyl-but-3-yn-2-ol (–78° C.)) was added dropwise at low temperature to a 10% THF solution of the monoprotected acetylene (1.0 mol.-equiv.). After 20 minutes at low temperature, a 10% THF soln. of the corresponding aldehydes 2 or 3 (1.0 mol.-equiv.) was added dropwise and after 20 minutes the temperature was equilibrated to 20° C. for 1.5 hours. After addition of a saturated aqueous solution of NH$_4$Cl, the reaction mixture was extracted with Et$_2$O, the organic phase was dried (Na$_2$SO$_4$), concentrated and purified by CC/SiO$_2$ (cyclohexane/AcOEt 95:5) to afford a mixture of diastereoisomers for analysis.

1-((1RS,2RS,4SR)-2-methyl-3-methylenebicyclo[2.2.1]hept-5-en-2-yl)-3-(trimethylsilyl)prop-2-yn-1-ol (22d)

Obtained in 53% yield from 2 as a 3:1 mixture of diastereoisomers at the carbinolic centre.
$^1$H-NMR: 0.21 (s, 9H); 1.11 (s, 3H); 1.54 (d, J=10, 1H); 1.81 (d, J=10, 1H); 2.02 (d, J=7, 10H); 2.88 (brs, 1H); 3.21 (brs, 1H); 4.40 (d, J=7, 1H); 4.87 (s, 1H); 5.03 (s, 1H); 6.16-6.24 (m, 2H).
$^{13}$C-NMR: 156.7 (s); 136.6 (2d); 106.0 (t); 105.2 (s); 90.8 (s); 69.0 (d); 52.5 (d); 50.7 (d); 50.6 (s); 47.1 (t); 19.7 (q); –0.2 (3q).

4-methyl-1-((1RS,2SR,4SR)-2-meth-3-methylenebicyclo[2.2.1]hepan-2-yl)pent-2-yne-1,4-diol (4c)

obtained in 47% yield from 3 as a 80:20 mixture of stereoisomer at the carbinolic centre.
$^1$H-NMR: 1.19 (s, 3H); 1.19-1.31 (m, 2H); 1.41-1.50 (m, 1H); 1.54 (s, 6H); 1.67-1.78 (m, 3H); 2.27 (brd, J=4, 1H); 2.33 (brs, 10H); 2.37 (brs, 10H); 2.72 (brd, J=4, 1H); 4.29 (s, 1H); 4.75 (s, 1H); 4.91 (s, 1H).
$^{13}$C-NMR: 161.7 (s); 103.9 (t); 90.5 (s); 81.0 (s); 66.5 (d); 65.2 (s); 50.2 (s); 47.2 (d); 45.4 (d); 36.7 (t); 31.4 (2q); 30.5 (t); 23.5 (t); 16.9 (q).

Compound 4 was obtained in 56% yield by deprotecting the above compounds according to J. Org. Chem., 2010, 22, 4306.

Example 2

Preparation of a Compound (IV)

Scheme 3:

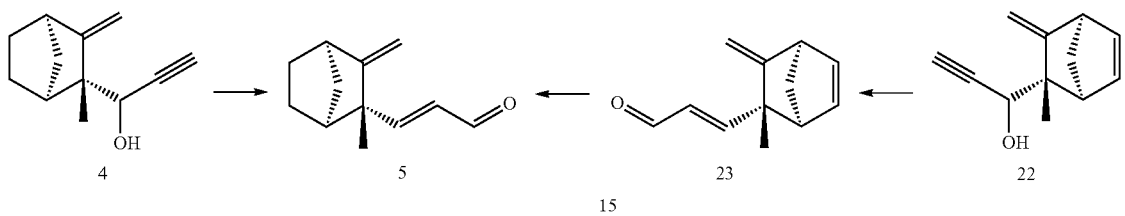

Compounds (IV) with the Dotted Line Representing a C—C (E)-3-((1SR,2SR,4RS)-2-methyl-3-methylenebicyclo[2.2.1]heptan-2-yl)acrylaldehyde 5

A mixture of alcohol 4 (100 mg, 0.521 mmol), p-Toluic acid (12.05 mg, 0.089 mmol), CuCl (1.03 mg, 10.4 μmol), and Ti(OnBu)$_4$ (2.3 mg, 6.77 mop, xylene (5 ml), was heated to 150° C. for 1 hour. The cold mixture was poured onto H$_2$O, washed with brine, extracted with ether and the solvents were evaporated, obtaining 100 mg of a yellow oil. Purification over a 12 g SiO$_2$ cartridge with cyclohexane/AcOEt 98:2 afforded 5 in 60% yield.

Alternatively, a mixture of alcohol 4 (150 mg, 0.851 mmol), [V$_2$O$_6$SiPh$_2$]$_n$ (7.5 mg, 0.024 mmol) in xylene (5 ml) was heated at 145° C. for 28 hours. The cold mixture was filtered through Celite, and the solvent was evaporated, the crude product (125 mg, 58:42 E/Z) was purified over a 12 g SiO$_2$ cartridge with cyclohexane/AcOEt 98:2 to afford 5 in 43% yield.

Alternatively 5 was also obtained in 69% isolated yield by hydrogenation of 23 (1.0-mol-equiv. of H$_2$) over Raney-Ni (5% by weight) at 0° in EtOH/H$_2$O 95:5. (93% based on recovered SM).

For analyses of 5, see C. Fehr et al. to Firmenich S A WO2009/141781 (2009 Nov. 26).

Compounds (IV) with the Dotted Line Representing a C=C (E)-3-((1RS,2SR,4SR)-2-methyl-3-methylenebicyclo[2.2.1]hept-5-en-2-yl)acrylaldehyde 23

A mixture of propargylic alcohol 22 (1000 mg, 5.74 mmol) and CpRuCl(PMe$_3$)$_2$ (123 mg, 0.344 mmol, T. Suzuki, M. Tokunaga, Y. Wakatsuki, *Tetrahedron Letters* 2002, 43, 7531) in iPrOH (15 ml) and H$_2$O (4.5 ml) was heated at 100° for 72 hrs. The cold reaction mixture was evaporated under vacuum, diluted with pentane, dried (Na$_2$SO$_4$) and purified by CC/SiO$_2$ with cyclohexane/AcOEt 9:1 to afford 23 in 60% yield, as a 95:5 E/Z mixture.

$^1$H-NMR: 9.55 (d, J=7.5, 1H); 6.95 (d, J=15.6, 1H); 6.20 (dd, J=7.5, 15.6, 1H); 6.20 (m, 2H); 5.14 (s, 1H); 4.70 (s, 1H); 3.27 (s, 1H); 2.77 (s, 1H); 1.68 (dt, J=8.6, 1.6, 1H); 1.62 (dt, J=8.6, 1.6, 1H); 1.16 (s, 3H).

$^{13}$C-NMR: 194.4 (d); 165.7 (d); 155.6 (s); 136.9 (d); 135.3 (d); 130.7 (d); 106.4 (t); 52.0 (d); 51.9 (d); 50.1 (s); 48.0 (t); 25.6 (q).

Example 3

Preparation of a Compound (V) and β-Santalol

Scheme 4:

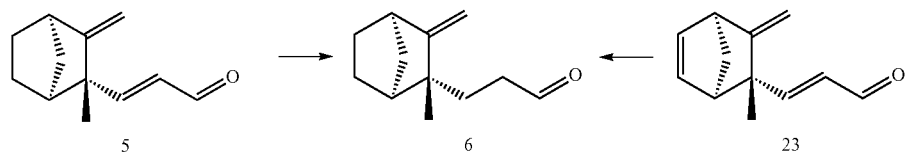

3-((1SR,2RS,4RS)-2-methyl-3-methylenebicyclo[2.2.1]heptan-2-yl)propanal 6

Obtained in 85% yield by hydrogenation of 23 (2.0-mol-equiv. of H$_2$) over Raney-Ni (5% by weight) at 0° in EtOH/H$_2$O 95:5. (90% based on the recovered SM). For analyses, see H. Sonawane, R. Harikisan, N. S. Bellur, J. R. Ahuja, D. J. Kulkarni, *J. Org. Chem.* 1991, 56, 1434; M. Saito, M. Kawamura, K. Ogasawara, *Tetr. Lett.* 1995, 36, 9003; D. Solas, J. Wolinsky, *J. Org. Chem.* 1983, 48, 1988; P. A. Christenson, B. J. Willis, *J. Org. Chem.* 1979, 44, 2012.

3-((1SR,2RS,4RS)-2-methyl-3-methylenebicyclo[2.2.1]heptan-2-yl)propanal 6

Obtained in 85% yield from 5 by hydrogenation over 5% Pd/CaCO$_3$ (5%), MeOH/H$_2$O (96:4) according to C. Fehr, I. Magpantay, J. Arpagaus, X. Marquet, M. Vuagnoux, *Angew. Chem. Intl. Ed.* 2009, 48, 7221. For analyses, see H. Sonawane, R. Harikisan, N. S. Bellur, J. R. Ahuja, D. J. Kulkarni, *J. Org. Chem.* 1991, 56, 1434; M. Saito, M. Kawamura, K. Ogasawara, *Tetr. Lett.* 1995, 36, 9003; D. Solas, J. Wolinsky, *J. Org. Chem.* 1983, 48, 1988; P. A. Christenson, B. J. Willis, *J. Org. Chem.* 1979, 44, 2012.

Compound 6 is then converted into β-santalol following the same procedure described in WO 09/141,781 by Fehr et al. (i.e compound of formula (V)→formula (VI)→formula (VII)→β-santalol).

A comparison of the whole yields obtained with the invention's process and those obtained according to the closest prior art documents demonstrates the efficiency of the invention's process, see Scheme 5:

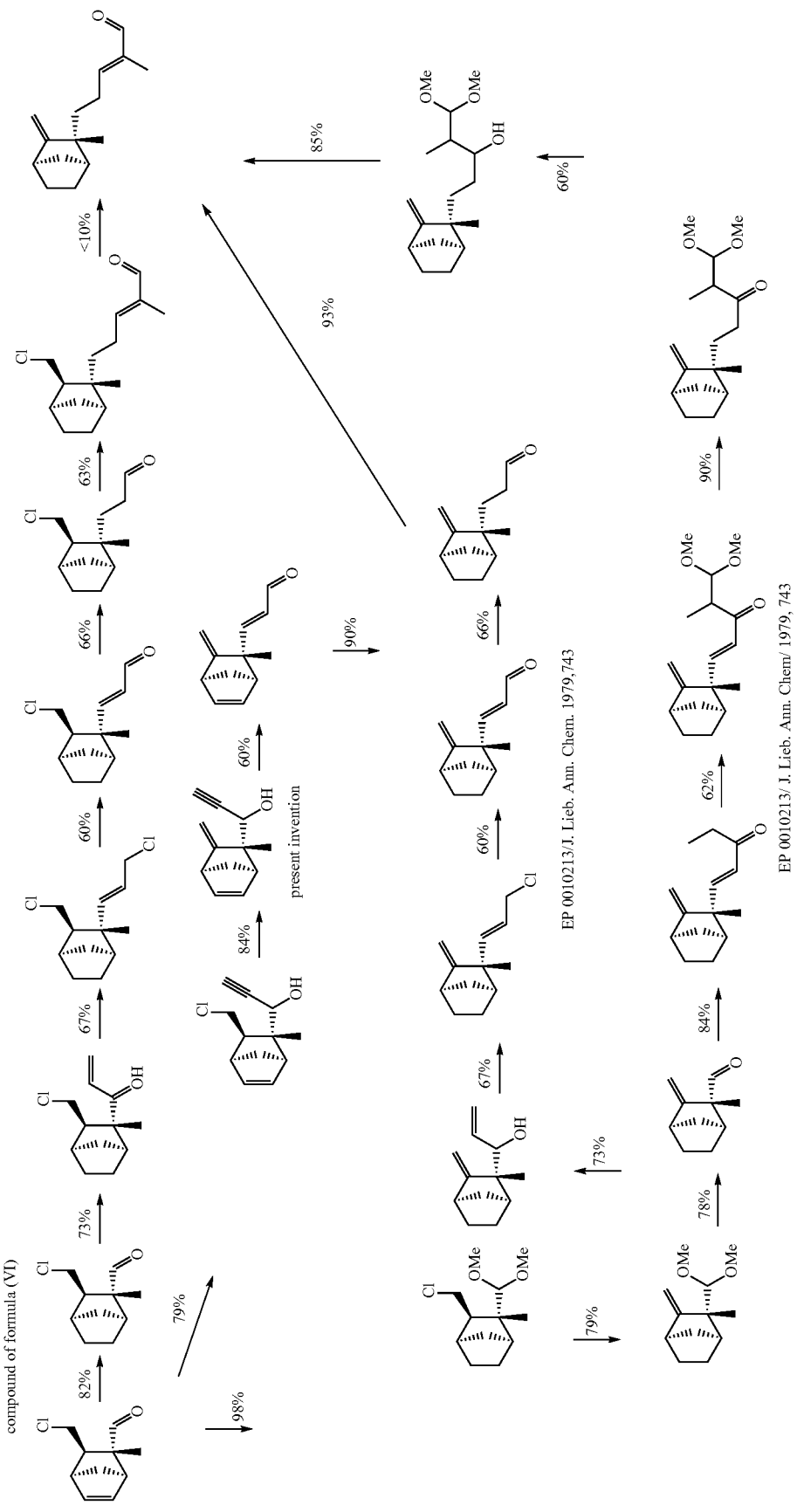
Scheme 5: Comparison of the yield using different process and starting from the same intermediate 12 and arriving at the same compound of formula (VI)

Global Yields:
Present invention: 33% (X=Cl) or 38% (X=Br)
EP10213/*J. lieb. Ann. Chem:* <11-15%
U.S. Pat. No. 4,197,411: <2%

Example 4

Preparation of the Optically Active Compounds (IV)

The asymmetric Diels-Alder reactions using dienophiles of type 11a,b (see Scheme 6) may be performed using the methodologies described by Corey et al. from −95° C. to −40° C.: *Org. Lett.* 2010, 12, 1836; *J. Am. Chem. Soc.* 2007, 129, 1498 (oxazaborolidines quaternized with AlBr$_3$); *Tetrahedron* 2006, 62, 11397; *J. Am. Chem. Soc.* 2006, 128, 1346; *J. Am. Chem. Soc.* 2006, 128, 740; *J. Am. Chem. Soc.* 2004, 126, 13708; *Org. Lett.* 2003, 5, 3979; *Org. Lett.* 2003, 5, 2465; *J. Am. Chem. Soc.* 2002, 124, 9992 (oxazaborolidines protonated with TfOH or Tf$_2$NH); *J. Am. Chem. Soc.* 1996, 118, 5502.

SCHEME 6
Diels-Alder reactions using dienophiles of
type 11a,b (e.e. of compound 12)

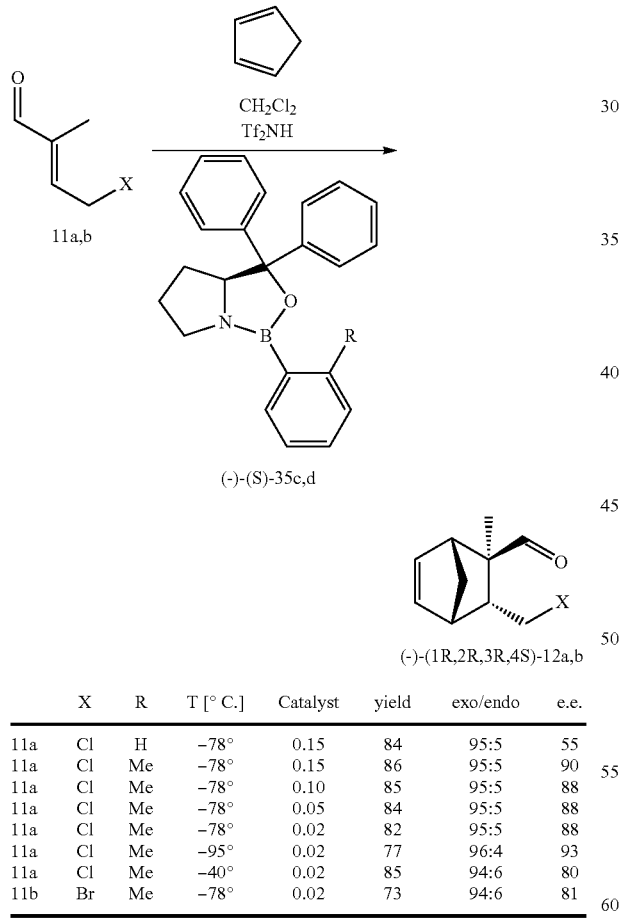

| | X | R | T [° C.] | Catalyst | yield | exo/endo | e.e. |
|---|---|---|---|---|---|---|---|
| 11a | Cl | H | −78° | 0.15 | 84 | 95:5 | 55 |
| 11a | Cl | Me | −78° | 0.15 | 86 | 95:5 | 90 |
| 11a | Cl | Me | −78° | 0.10 | 85 | 95:5 | 88 |
| 11a | Cl | Me | −78° | 0.05 | 84 | 95:5 | 88 |
| 11a | Cl | Me | −78° | 0.02 | 82 | 95:5 | 88 |
| 11a | Cl | Me | −95° | 0.02 | 77 | 96:4 | 93 |
| 11a | Cl | Me | −40° | 0.02 | 85 | 94:6 | 80 |
| 11b | Br | Me | −78° | 0.02 | 73 | 94:6 | 81 |

Alternatively, the asymmetric Diels-Alder reactions using dienophiles of type 11a,b may be performed using the methodologies of:

Either T. Kaino, Y. Tanaka, K. Osawa, T. Yurino, K. Maruoka, *Chem. Commun.* 2009, 1956, with BINAM derivatives at 0° C.; or, K. Ishihara, H. Kurihara, M. Matsumoto, H. Yamamoto, *J. Am. Chem. Soc.* 1998, 120, 6920, with BINOL and bonnie acid derivatives at −78° C. (See also H. Yamamoto et al. *J. Am. Chem. Soc.* 1994, 116, 1561; *J. Org. Chem.* 1989, 54, 1481; *Tetrahedron Lett.* 1989, 30, 7231), or Rawal et al. *Tetrahedron Lett.* 2007, 48, 1265; *J. Am. Chem. Soc.* 2002, 124, 5950; *Org. Lett.* 2002, 4, 1163; *J. Am. Chem. Soc.* 2000, 122, 7843, using Jacobsen's chromium SALEN.

By applying the same experimental procedure as described above:

(−)-(1S,2R,3R,4R)-13a was obtained from (−)-(1S,2R,3R,4R)-12a via hydrogenation with Pd/C with a yield of 87% ((−)-(1S,2R,3R,4R)-13a: $[\alpha]_D^{20}$=−17.4, c=3.50 CHCl$_3$);

(−)-(1S,2R,3R,4R)-14a was obtained from (−)-(1S,2R,3R,4R)-13a and ethynylmagnesium with a yield of 68% ((−)-(1S,2R,3R,4R)-14a: $[\alpha]_D^{20}$=−4.5, c=1.7 CHCl$_3$);

(−)-(1S,2R,4R)-4 was obtained from (−)-(1S,2R,3R,4R)-14a and tBuOK with a yield of 78% ((−)-(1S,2R,4R)-4: $[\alpha]_D^{20}$=−59.6, c=0.90 CHCl$_3$);

(−)-(1S,2S,4R)-5 was obtained from (−)-(1S,2R,4R)-4 and 5% (Ph2SiOVMe2O)$_n$, (xylene, 140°) with a yield of 45% ((−)-(1S,2S,4R)-5: $[\alpha]_D^{20}$=$[\alpha]_D^{20}$=−97.4, c=0.40 CHCl$_3$).

What is claimed is:

1. A compound of formula

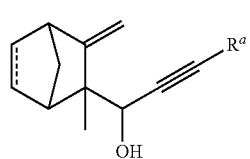

(I)

in the form of any one of its stereoisomers or mixtures thereof, wherein the dotted line represents a carbon-carbon single or double bond, and R$^a$ represents a hydrogen atom or a Si(R$^b$)$_3$ or (R$^b$)$_2$COH group, each R$^b$ representing C$_{1-6}$ alkyl group or a phenyl group.

2. A compound of formula

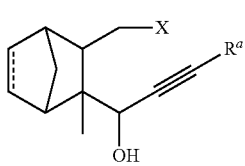

(II)

in the form of any one of its stereoisomers or mixtures thereof, wherein the dotted line and R$^a$ have the same meaning as in claim 1, and X represents a halogen atom, a C$_{1-4}$ acyl group, a C$_{1-4}$ alkoxyl group, phenyl sulfonate optionally substituted by one or two C$_{1-3}$ alkyl groups, or a C$_{1-4}$ alkyl sulfonate, or a group of formula OC(=O)OR$^c$, wherein R$^c$ is a C$_1$-C$_7$ alkyl group.

3. A compound according to claim 2, wherein X may represent a halogen atom or a sulfonate group as defined in claim 2.

4. A compound according to claim 1, wherein R$^a$ represents a hydrogen atom or a Si(R$^b$)$_3$, each R$^b$ representing a C$_{1-4}$ alkyl group or a phenyl group.

5. A compound according to claim 1, wherein said compound is in the form of a mixture of stereoisomers comprising more than 50% (w/w) of:

the (1RS,4SR) or the (1RS,2SR,4SR) diastereoisomer, when the dotted line represents a single bond; or the (1RS,4SR) or the (1RS,2RS,4SR) diastereoisomer, when the dotted line represents a double bond.

6. A compound according to claim 1, wherein said compound is in the form of a mixture of stereoisomers comprising more than 50% (w/w) of the (1S,4R) or (1S,2R,4R) enantiomer, when the dotted line represents a single bond; or the (1R,4S) or (1R,2R,4S) enantiomer, when the dotted line represents a double bond.

7. A process for the preparation of a compound of formula (I), as defined in claim 1, comprising the following steps:

a) reacting a compound of formula:

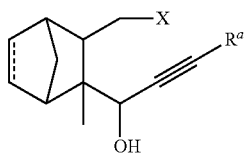

(II)

with a base having a $pK_a$ above 16 wherein $R^a$ represents a hydrogen atom or a $Si(R^b)_3$ or $(R^b)_2COH$ group, each $R^b$ representing $C_{1-6}$ alkyl group or a phenyl group;

b) optionally, when $R^a$ is not a hydrogen atom, treating the compound obtained in step a) with a suitable base or a fluorine salt to obtain compound (I) wherein $R^a$ is hydrogen atom.

8. A method of preparation of a compound of formula

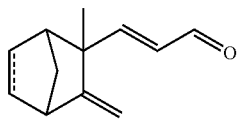

(IV)

in the form of any one of its stereoisomers or mixtures thereof, and wherein the dotted represents a carbon-carbon single or double bond);

said method comprising:
1) reacting a compound (I-a)

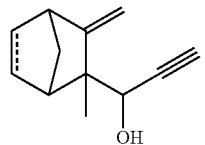

(I-a)

in the form of any one of its stereoisomers or mixtures thereof, wherein the dotted represents a carbon-carbon single or double bond line has the same meaning as in formula (I);

with a complex selected amongst:

a vanadyl derivative of formula $[V_2O_6SiPh_2]_n$ or $(Ph_3SiO)_3VO$ wherein Ph represents a phenyl group optionally substituted by one or two methyl groups, and n indicates that the compound is a monomeric, oligomeric or polymeric form;

a Ru complex of formula $[CpRuCl(PR_3)]$, wherein Cp indicates a cyclopentadienyl optionally substituted by one to five $C_{1-2}$ alkyl groups, and R represents $C_{1-5}$ alkyl groups or a phenyl group optionally substituted by one or two methyl groups; or mixture of a cuprous halide, a $Ti(OR)_4$ salt wherein R is as defined above, and a $C_{1-10}$ carboxylic acid; and 2) optionally hydrogenating the compound of formula

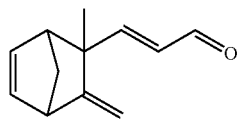

(IV')

in the form of any one of its stereoisomers or mixtures thereof;

into a compound of formula

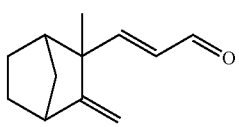

(IV'')

in the form of any one of its stereoisomers or mixtures thereof.

* * * * *